Figure 1:
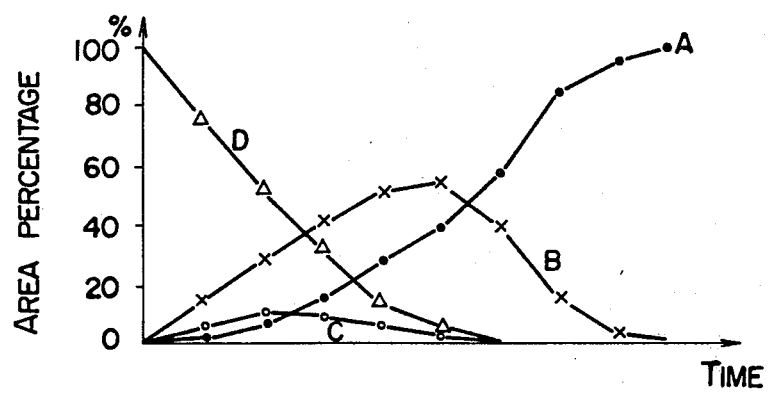

United States Patent [19]

Nishikuri et al.

[11] 4,292,247
[45] Sep. 29, 1981

[54] PROCESS FOR PRODUCING ANTHRAQUINONE INTERMEDIATES

[75] Inventors: Masao Nishikuri, Hirakata; Akira Takeshita, Toyonaka; Hirohito Kenmochi, Takatsuki, all of Japan

[73] Assignee: Sumitomo Chemical Company, Limited, Osaka, Japan

[21] Appl. No.: 898,667

[22] Filed: Apr. 21, 1978

[30] Foreign Application Priority Data

Apr. 25, 1977 [JP] Japan ................................. 52-48091
Apr. 26, 1977 [JP] Japan ................................. 52-48839

[51] Int. Cl.³ ...................... C07C 97/26; C07C 97/25
[52] U.S. Cl. .................................... 260/381; 260/380
[58] Field of Search ............................... 260/380, 381

[56] References Cited

U.S. PATENT DOCUMENTS 4,197,250  4/1980  Redeker et al. ..................... 260/380

*Primary Examiner*—Charles F. Warren
*Assistant Examiner*—Raymond K. Covington
*Attorney, Agent, or Firm*—Stevens, Davis, Miller & Mosher

[57] ABSTRACT

1-Amino-2,4-dibromoanthraquinone, which can be hydrolyzed to produce 1-amino-2-bromo-4-hydroxyanthraquinone which is an intermediate for the production of dyes, is produced by bromination of 1-aminoanthraquinone in a concentrated sulfuric acid at a temperature of 50° to 150° C.

12 Claims, 2 Drawing Figures

PROCESS FOR PRODUCING ANTHRAQUINONE INTERMEDIATES

The present invention relates to a process for producing anthraquinone series intermediates particularly useful in the dye industry. More particularly, it relates to a process for producing 1-amino-2,4-dibromoanthraquinone by bromination of 1-aminoanthraquinone and also to a process for producing 1-amino-2-bromo-4-hydroxyanthraquinone by hydrolysis of said 1-amino-2,4-dibromoanthraquinone.

As a process for producing 1-amino-2-bromo-4-hydroxyanthraquinone, the following ones are well known: Hydrolysis of 1-amino-2,4-dibromoanthraquinone in a concentrated sulfuric acid or fuming sulfuric acid in the presence of boric acid (PB Report No. 86139, page 5; U.S. Pat. No. 2,604,480), bromination of 1-amino-4-hydroxyanthraquinone (Yūki Gōsei Kagaku Kyōkai-shi, Vol. 17, page 140), and ring closure of 3'-nitro-4'-bromobenzoyl benzoic acid (Japanese Patent Kokai (Laid-Open) No. 68626/1973). The second and third processes are not advantageous industrially since synthesis of the precursor is not easy as compared with the first one.

As a process for producing 1-amino-2,4-dibromoanthraquinone, the following ones are well known: Dibromination of 1-aminoanthraquinone-2-sulfonic acid in an aqueous solvent (J. Chem. Soc. 1939, page 816; U.S. Pat. No. 2,169,196), dibromination of 1-aminoanthraquinone in an inert organic solvent (Ber., 49, 2165; British Pat. No. 1,239,778), and a process which comprises dissolving 1-aminoanthraquinone in sulfuric acid, and discharging the solution into water thereby dispersing 1-aminoanthraquinone in a finely divided form, followed by dibromination in the aqueous medium (PB Report No. 86139, page 6; Ullmanns Encyclopädie der technischen Chemie, 4 Aufl., Band 7, page 597).

The process comprising dibromination of 1-aminoanthraquinone-2-sulfonic acid has the following drawbacks: The process comprises two steps, i.e., sulfonation of 1-aminoanthraquinone and dibromination of the resulting 1-aminoanthraquinone-2-sulfonic acid when 1-aminoanthraquinone is used as a starting material, and since the dibromination is carried out in an aqueous medium, the resulting dibromo-compound needs to be isolated by filtration and drying for subjecting it to the subsequent hydrolysis.

The process comprising dibromination of 1-aminoanthraquinone in an inert organic solvent also has the following drawbacks: Since the solvent used in the dibromination step is different from that used in hydrolysis of the resulting dibromo-compound, the compound needs to be isolated by filtration or extracted with sulfuric acid from the inert organic solvent, whereby the operation becomes very troublesome.

Further, the process comprising dibromination of finely dispersed 1-aminoanthraquinone in an aqueous medium also has the following drawbacks: This process requires a step of dispersing 1-aminoanthraquinone comprising dissolution of 1-aminoanthraquinone in sulfuric acid and discharge of the resulting solution into water and a step of dibromination, the resulting dibromo-compound needs to be isolated for subjecting it to hydrolysis thereby producing 1-amino-2-bromo-4-hydroxyanthraquinone, and therefore filtration and drying steps become necessary, and the dibromo-compound obtained by this process contains 2 to 4% by weight of unreacted 1-amino-2-bromoanthraquinone since 1-aminoanthraquinone is reacted with bromine in the state of suspension rather than solution in the aqueous medium, and therefore this monobromo-derivative undesirably forms an impurity of the product in the subsequent step, for example, hydrolysis step.

The inventors extensively studied to develop industrially advantageous processes for producing 1-amino-2,4-dibromoanthraquinone and 1-amino-2-bromo-4-hydroxyanthraquinone not having the aforesaid drawbacks. As a result, it has been found that 1-amino-2,4-dibromoanthraquinone is obtained in a high purity and a high yield by brominating 1-aminoanthraquinone in a concentrated sulfuric acid with heating and that the above bromination reaction mixture as it is (without the aforesaid troublesome step of isolating the dibromoanthraquinone) is subjected to hydrolysis in the presence of boric acid, if necessary, after controlling the sulfuric acid concentration of the mixture with a fuming sulfuric acid, sulfuric anhydride or chlorosulfonic acid, whereby the desired 1-amino-2-bromo-4-hydroxyanthraquinone is obtained in a high yield.

The present invention provides a process for producing 1-amino-2,4-dibromoanthraquinone, which comprises reacting 1-aminoanthraquinone with a brominating agent in a concentrated sulfuric acid under heating, and also provides a process for producing 1-amino-2-bromo-4-hydroxyanthraquinone, which comprises reacting 1-aminoanthraquinone with a brominating agent in a concentrated sulfuric acid under heating, and then subjecting the resulting 1-amino-2,4-dibromoanthraquinone-containing reaction mixture to hydrolysis in the presence of boric acid.

Figure 2:
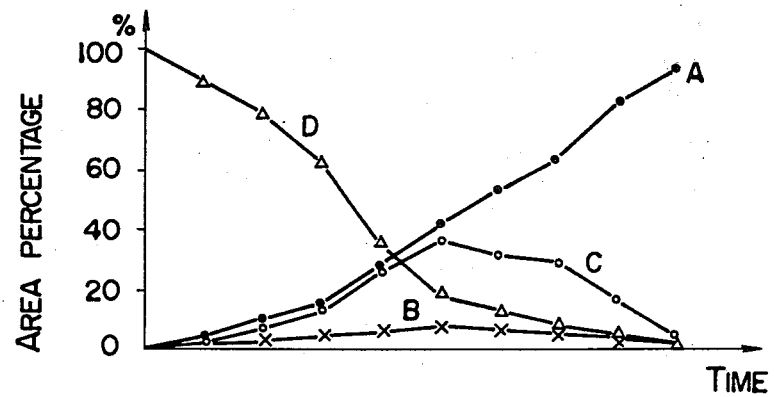

In the accompanying drawing, FIGS. 1 and 2 show a change in the composition of the reaction mixture with the lapse of time in the synthesis of 1-amino-2,4-dibromoanthraquinone according to Example 1 of the present invention and Referential Example (PB Report No. 86139, page 6), respectively, obtained by analyzing by gas chromatography the cakes which were sampled in the course of the synthesis and expressing the weight ratios of the respective components contained in the cakes by way of area percentage. In these figures, the curves A, B, C and D represent 1-amino-2,4-dibromoanthraquinone, 1-amino-4-bromoanthraquinone, 1-amino-2-bromoanthraquinone and 1-aminoanthraquinone, respectively.

In the present invention, the concentrated sulfuric acid used in the dibromination preferably has a concentration of 80 to 100% by weight, and more preferably has a concentration of 85 to 98% by weight. Particularly, when the reaction mixture from the dibromination is directly subjected to hydrolysis without isolating the produced dibromoanthraquinone, it is preferable to use a sulfuric acid concentration of 85% by weight or more. The dibromination can be effected even when sulfuric acid having a concentration of below 80% by weight is used, but it is inconvenient from an industrial viewpoint, because a large amount of fuming sulfuric acid, sulfuric anhydride or the like is inevitably required to control the concentration of sulfuric acid in the subsequent hydrolysis step. When the concentration is higher than 98% by weight, the rate of reaction tends to slow down and the amount of by-products formed tends to increase. The amount of sulfuric acid used is preferably 1 to 8 times the weight of 1-aminoanthraquinone. The brominating agent is bromine, hydrogen bromide or alkali metal bromides, and of these compounds preferred is bromine. The amount of bromine used is 1.0 to 3 moles per mole of 1-aminoanthraquinone and use of more than 3 moles is not advantageous economically. The dibromination temperature depends on the concentration of sulfuric acid and can be lowered with an increase in the concentration of sulfuric acid. It is usually 50° to 150° C., and it is desirable from an industrial viewpoint to add bromine dropwise at 80° to 130° C. The reaction time depends on the sulfuric acid concentration and reaction temperature, and it is generally 4 to 15 hours. The reaction may be carried out in the presence of a catalyst used in conventional bromination, for example, iodine, potassium iodide, zinc chloride or the like. Also, an organic solvent such as acetic acid and propionic acid or an inert solvent such as nitrobenzene may be added in order to increase the solubility of bromine.

According to the present invention, the reaction proceeds in the state wherein 1-aminoanthraquinone is in complete solution in a concentrated sulfuric acid, and therefore the desired compound can be obtained in a high purity with very little unreacted 1-amino-2-bromoanthraquinone and 1-amino-4-bromoanthraquinone. After completion of the dibromination, according to a conventional method, the reaction mixture can be diluted to deposit crystals, which are then collected by filtration and washed to obtain the desired dibromoanthraquinone.

In the bromination of finely dispersed 1-aminoanthraquinone in an aqueous medium according to the aforesaid prior art, the proportion of 1-amino-2,4-dibromoanthraquinone produced through 1-amino-2-bromoanthraquinone is overwhelmingly large. In the bromination according to the process of the present invention, however, it is important that the proportion of 1-amino-2,4-dibromoanthraquinone produced through 1-amino-4-bromoanthraquinone is fairly larger than that in the other cases, particularly when sulfuric acid of a higher concentration is used. This difference is shown in FIGS. 1 and 2. As is apparent from the figures, bromination in an aqueous dispersion medium is different in reaction mechanism from bromination in a concentrated sulfuric acid.

In the production of 1-amino-2-bromo-4-hydroxyanthraquinone according to the process of the present invention, 1-amino-2,4-dibromoanthraquinone thus obtained need not be isolated and the reaction mixture is subjected to hydrolysis as it is. The hydrolysis is carried out in a concentrated sulfuric acid having a concentration of preferably 95% by weight or more, or in fuming sulfuric acid. When the preceding dibromination is carried out in a concentrated sulfuric acid of 95% by weight or less, it is desirable to increase the sulfuric acid concentration, prior to the hydrolysis, with addition of sulfuric anhydride, fuming sulfuric acid or chlorosulfonic acid. Thereafter, boric acid is added thereto. The amount of boric acid used is preferably about 1 to about 3 moles per mole of the anthraquinone compound. The resulting mixture is kept at preferably within the range of 100° to 140° C., while being stirred, until the unreacted dibromoanthraquinone disappears usually for 3 to 10 hours. When the sulfuric acid concentration is low, the rate of hydrolysis is so low that a high-temperature and long-term reaction is necessary. Also, when the concentration of fuming sulfuric acid is too high, the amount of by-products formed tends to increase. After completion of the hydrolysis, according to a conventional method, the reaction mixture is diluted to deposit crystals, which are then collected by filtration and washed to obtain the desired 1-amino-2-bromo-4-hydroxyanthraquinone.

1-Amino-2,4-dibromoanthraquinone and 1-amino-2-bromo-4-hydroxyanthraquinone obtained by the process of the present invention are very valuable as intermediates for dyes. Accordingly, the industrial value of the present invention is very large.

The present invention will be illustrated with reference to the following examples, but the present invention is not limited to these examples. In the examples, all parts and % are expressed by weight unless otherwise indicated.

EXAMPLE 1

A mixture of 100 parts of 94% sulfuric acid and 20 parts of 1-aminoanthraquinone was heated to 100° C., and 28.7 parts of bromine was added dropwise over 5 hours at the same temperature. The reaction mixture was kept at the same temperature for further 5 hours, cooled to room temperature and discharged into 500 parts of water containing 4.6 parts of sodium bisulfite. The precipitated crystals were filtered, washed and dried to obtain 34 parts of a cake having a melting point of 224° to 226° C. This melting point agreed very well with that of 1-amino-2,4-dibromoanthraquinone, 226° C., disclosed in the literature. Further, the results of elementary analysis agreed approximately with the calculated values as shown below.

|  | C % | H % | N % | Br % |
|---|---|---|---|---|
| Calculated (as $C_{14}H_7NO_2Br_2$) | 44.13 | 1.85 | 3.68 | 41.95 |
| Found | 44.10 | 1.84 | 3.72 | 41.62 |

The purity of the product was analyzed to obtain the following results: 1-Amino-2,4-dibromoanthraquinone 95.0%; 1-amino-2-bromoanthraquinone 0.1%; 1-amino-4-bromoanthraquinone 0.4%.

EXAMPLE 2

A mixture of 100 parts of 90% sulfuric acid, 20 parts of 1-aminoanthraquinone and 0.1 part of potassium iodide was heated to 120° C., and 30 parts of bromine was added dropwise over 6 hours at the same temperature. The reaction mixture was kept at the same temperature for further 2 hours, cooled to 50° C. and discharged into 500 parts of water containing 5 parts of sodium bisulfite. The precipitated crystals were filtered, washed and dried to obtain 33.8 parts of a 1-amino-2,4-dibromoanthraquinone cake (m.p. 223°–225° C.).

EXAMPLE 3

A mixture of 160 parts of 96% sulfuric acid and 20 parts of 1-aminoanthraquinone was heated to 80° C., and at the same temperature a mixture of 20 parts of bromine and 5 parts of acetic acid was added dropwise over 3 hours. The reaction mixture was kept at the same temperature for further 3 hours. Thereafter, a mixture of 15 parts of bromine and 4 parts of acetic acid was added dropwise to the reaction mixture over 2 hours, and the mixture was kept at the same temperature for further 2 hours. The mixture was then kept at 100° C. for 3 hours, cooled to room temperature and discharged into 1000 parts of water containing 7 parts of sodium bisulfite. The precipitated crystals were filtered, washed and dried to obtain 34.2 parts of the same 1-amino-2,4-dibromoanthraquinone cake as in Example 1.

EXAMPLE 4

A mixture of 100 parts of 94% sulfuric acid and 20 parts of 1-aminoanthraquinone was heated to 100° C., and 28.7 parts of bromine was added dropwise over 5 hours at the same temperature. The reaction mixture was kept at the same temperature for further 5 hours and cooled to room temperature. Thereafter, 11 parts of boric acid and 100 parts of 28% fuming sulfuric acid were added to the reaction mixture which was then heated to 120° C. The mixture was kept at the same temperature until unreacted 1-amino-2,4-dibromoanthraquinone was no longer detected. It took about 5 hours until that time. After the reaction was finished, the reaction mixture was cooled to room temperature and discharged into 1000 parts of water. The precipitated crystals were filtered, washed and dried to obtain 28.5 parts of a cake having a melting point of 228°–232° C. This melting point agreed approximately with that of 1-amino-2-bromo-4-hydroxyanthraquinone, 231°–232° C., disclosed in the literature. Further, the results of elementary analysis also agreed approximately with the calculated values as shown below.

|  | C % | H % | N % | Br % |
| --- | --- | --- | --- | --- |
| Calculated (as $C_{14}H_8NO_3Br$) | 52.86 | 2.53 | 4.40 | 25.12 |
| Found | 52.90 | 2.51 | 4.37 | 24.93 |

EXAMPLE 5

A mixture of 100 parts of 90% sulfuric acid, 20 parts of 1-aminoanthraquinone and 0.1 part of potassium iodide was heated to 120° C., and 30 parts of bromine was added dropwise over 6 hours at the same temperature. The reaction mixture was kept at the same temperature for further 2 hours and cooled to room temperature. Thereafter, 7 parts of boric anhydride and 70 parts of 65% fuming sulfuric acid were added to the reaction mixture which was then heated to 120° C. and kept at the same temperature for 6 hours. After the reaction was finished, the reaction mixture was cooled to 90° C., and 115 parts of water was added dropwise thereto at 90° to 100° C. over 2 hours, followed by filtration at 55° C. The filtered cake was washed with 100 parts of 60% sulfuric acid and then water and dried to obtain 27 parts of a 1-amino-2-bromo-4-hydroxyanthraquinone cake (m.p. 231°–233° C.).

EXAMPLE 6

A mixture of 160 parts of 96% sulfuric acid and 20 parts of 1-aminoanthraquinone was heated to 80° C., and at the same temperature a mixture of 20 parts of bromine and 5 parts of acetic acid was added dropwise over 3 hours. The reaction mixture was kept at the same temperature for further 3 hours. Thereafter, a mixture of 15 parts of bromine and 4 parts of acetic acid was added dropwise to the reaction mixture over 2 hours, and the mixture was kept at the same temperature for further 2 hours. The mixture was then kept at 100° C. for 3 hours and cooled to room temperature. Thereafter, 10 parts of boric acid was added to the reaction mixture which was then kept at 130° C. for 8 hours. Eighty parts of water was added dropwise at 90° to 100° C. over 2 hours to the mixture which was then cooled to 55° C. and filtered. The filtered cake was washed with 100 parts of 60% sulfuric acid and then water and dried to obtain 25.5 parts of the same 1-amino-2-bromo-4-hydroxyanthraquinone cake as in Example 1.

Referential Example (Aqueous dispersion process in PB Report No. 86139)

Twenty parts of 1-aminoanthraquinone was completely dissolved at 40° C. in a mixture of 16 parts by volume of 96% sulfuric acid and 18 parts by volume of 20% fuming sulfuric acid. The solution was cooled to 25° C. and discharged into 320 parts of water. Thereafter, 15.9 parts of bromine was added dropwise at 25° C. to the aqueous dispersion and then 6.5 parts of chlorine gas was introduced thereinto over 7 hours. The aqueous dispersion was then heated to 50° C. over 3 hours and kept at the same temperature for 2 hours. The dispersion was then heated to 70° C. over 2 hours and kept at 80° C. for further 1 hour. After adding 1 part by volume of an aqueous sodium bisulfite solution to the dispersion, the precipitate was filtered, washed and dried to obtain 33.2 parts of a product. The purity of the product was analyzed to obtain the following results: 1-Amino-2,4-dibromoanthraquinone 92.5%; 1-amino-2-bromoanthraquinone 3.0%; 1-amino-4-bromoanthraquinone a trace amount.

What is claimed is:

1. A process for producing 1-amino-2-bromo-4-hydroxyanthraquinone, which comprises:
   (1) dissolving 1-aminoantrhaquinone in a concentrated sulfuric acid, the concentration of sulfuric acid being 90 to about 98% by weight,
   (2) adding a brominating agent into the resulting solution at a temperature of 50° to 150° C.,
   (3) stirring the mixture to convert 1-aminoanthraquinone into 1-amino-2, 4-dibromoanthraquinone at the same temperature as defined above,
   (4) controlling the concentration of sulfuric acid in the reaction mixture to 95% by weight or more, and
   (5) stirring the 1-amino-2, 4-dibromoanthraquinone-containing reaction mixture at a temperature of 100° to 140° C. in the presence of boric acid to convert 1-amino-2, 4-dibromoanthraquinone into 1-amino-2-bromo-4-hydroxyanthraquinone.

2. The process according to claim 1, wherein the brominating agent is bromine, hydrogen bromide or an alkali metal bromide.

3. The process according to claim 1, wherein the amount of the brominating agent is 1.0 to 3 moles per mole of 1-aminoanthraquinone.

4. The process according to claim 1, wherein the amount of the concentrated sulfuric acid is 1 to 8 times the weight of 1-aminoanthraquinone.

5. The process according to claim 1, wherein the controlling is effected using sulfuric anhydride, fuming sulfuric acid or chlorosulfonic acid.

6. The process according to claim 1, wherein the brominating agent is bromine.

7. The process according to claim 1, wherein the adding in the step (2) is carried out at a temperature of 80° to 130° C.

8. A process for producing 1-amino-2, 4-dibromoanthraquinone which comprises:
   (1) dissolving 1-aminoanthraquinone in a concentrated sulfuric acid, the concentration of sulfuric acid being 90 to about 98% by weight, (2) adding a brominating agent into the resulting solution at a temperature of 50° to 150° C., and (3) stirring the mixture to convert 1-aminoanthraquinone into a 1-amino-2, 4-dibromoanthraquinone at the same temperature as defined above.

9. The process according to claim 8, wherein the brominating agent is bromine, hydrogen bromide or an alkali metal bromide.

10. The process according to claim 8, wherein the amount of the brominating agent is 1.0 to 3 moles per mole of 1-aminoanthraquinone.

11. The process according to claim 8, wherein the amount of the concentrated sulfuric acid is 1 to 8 times the weight of 1-aminoanthraquinone.

12. The process according to claim 8, wherein the adding is carried out at a temperature of 80° to 130° C.

* * * * *